(12) United States Patent
Zhang et al.

(10) Patent No.: US 11,454,112 B2
(45) Date of Patent: Sep. 27, 2022

(54) SYSTEM AND METHOD OF TYPING HETEROGENEOUS RESERVOIR ROCKS

(71) Applicant: SAUDI ARABIAN OIL COMPANY, Dhahran (SA)

(72) Inventors: Ming Zhang, Beijing (CN); Hongwen Zhao, Beijing (CN); Yufeng Cui, Beijing (CN); David Amendt, Dhahran (SA); Peng Lu, Dhahran (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 235 days.

(21) Appl. No.: 16/836,694

(22) Filed: Mar. 31, 2020

(65) Prior Publication Data

US 2021/0301658 A1   Sep. 30, 2021

(51) Int. Cl.
| | |
|---|---|
| E21B 49/02 | (2006.01) |
| G01N 15/08 | (2006.01) |
| G01N 33/24 | (2006.01) |
| G01V 3/38 | (2006.01) |
| G01V 11/00 | (2006.01) |

(52) U.S. Cl.
CPC ......... *E21B 49/02* (2013.01); *G01N 15/0886* (2013.01); *G01N 33/241* (2013.01); *G01V 3/38* (2013.01); *G01V 11/002* (2013.01)

(58) Field of Classification Search
CPC ...... G01V 3/38; G01V 11/002; G01N 33/241; G01N 15/0886; E21B 49/02
See application file for complete search history.

(56) References Cited

U.S. PATENT DOCUMENTS

| | | |
|---|---|---|
| 2010/0040281 A1 | 2/2010 | Chen et al. |
| 2016/0124115 A1* | 5/2016 | Theologou ........... G01V 99/005 702/11 |
| 2017/0083608 A1 | 3/2017 | Ye et al. |
| 2017/0114619 A1 | 4/2017 | Conn et al. |
| 2017/0124115 A1 | 5/2017 | Duan et al. |
| 2018/0259661 A1 | 9/2018 | Harris |
| 2018/0347354 A1 | 12/2018 | Li et al. |
| 2019/0368994 A1* | 12/2019 | Al Readean ........... G01N 15/08 |

FOREIGN PATENT DOCUMENTS

| | | |
|---|---|---|
| WO | 2019118656 A1 | 6/2019 |
| WO | 2019164859 A1 | 8/2019 |

OTHER PUBLICATIONS

Bize-Forest, Carbonate Reservoir Rock Typing and the Link Between Routine Core Analysis and Special Core Analysis, SCA2014-049, Avignon, France, September (Year: 2014).*

(Continued)

*Primary Examiner* — Michael J Dalbo
(74) *Attorney, Agent, or Firm* — Osha Bergman Watanabe & Burton LLP (57) ABSTRACT

A method of rock typing includes obtaining mercury injection capillary pressure (MICP) data regarding a region of interest. A distance matrix is computed for distributions determined from the MICP data using a statistical distance metric. A cluster tree of the distributions is generated using the distance matrix. The cluster tree is adjusted based on a petrographic characteristic to produce an adjusted cluster tree, which is used to determine a pore structure types of the region of interest.

15 Claims, 8 Drawing Sheets

(56) References Cited

OTHER PUBLICATIONS

Sfidari, Prediction of pore facies using GMDH-type neural networks: a case study from the South Pars gas field, Persian Gulf basin, Geopersia 8 (1), 2018, pp. 43-60. (Year: 2018).*

Wang, Improved pore structure prediction based on MICP with a data mining and machine learning system approach in Mesozoic strata of Gaoqing field, Jiyang depression, Journal of Petroleum Science and Engineering 171 (2018) 362-393 (Year: 2018).*

Billard, Clustering in Contemporary Mixed-valued Data, Proceedings 59th ISI World Statistics Congress, Aug. 25-30, 2013, Hong Kong (Session IPS079) (Year: 2013).*

Wang, Ruyi et al., "Grid density overlapping hierarchal algorithm for clustering of carbonate reservoir rock types: A case from Mishrif Formation of West Qurna-1 oilfield, Iraq", Journal of Petroleum Science and Engineering, ScienceDirect, Elsevier B.V., vol. 182, No. 106209, Jun. 2019, pp. 1-19 (19 pages).

Wang, Xidong et al., "Improved pore structure prediction based on MICP with a data mining and machine learning system approach in Mesozioc strata of Gaoqing field, Jiyang depression", Journal of Petroleum Science and Engineering, ScienceDirect, Elsevier B.V., vol. 171, Jul. 2018, pp. 362-393 (32 pages).

International Search Report issued in corresponding International Application No. PCT/US2020/031807, dated Jan. 13, 2021 (3 pages).

Written Opinion issued in corresponding International Application No. PCT/US2020/031807, dated Jan. 13, 2021 6 pages).

Bize-Forest, N., Baines, V., Boyd, A., Moss, A., and Oliveira, R., 2014. "Carbonate reservoir rock typing and the link between routine core analysis and special core analysis", International Symposium of the Society of Core Analysts, pp. 8-11. (6 pages).

Johnson,S.C. 1967, "Hierarchical Clustering Schemes" Psychometrika, 2:241-254 (2 pages).

Kadkhodaie, A., Sefidari, E., Ahmadi, B., and Faraji MA., 2018. "Prediction of pore facies using GMDH-type neural networks" a case study from the South Pars gas field, Persian Gulf basin. Geopersia, 8(1): 43-60 (19 pages).

Palavecino, M. and Torres-Verdin, C., 2016. "New method of petrophysical rock classification based on MICP and grain-size distribution measurements". SPWLA 57th Annual Logging Symposium (7 pages).

Ramdas, A., Garcia, N., and Cuturi, M., 2017 "On Wasserstein two sample testing and related families of nonparametric tests". Entropy, 19(2): 47 (18 pages).

Rubner, Y., Tomasi, C., and Guibas, L.J., 2000. "The earth mover's distance as a metric for Image Retrieval" International Journal of Computer Vision, 40(2), pp. 99-121 (20 pages).

Washburn, E.W., 1921. "The Dynamics of Capillary Flow". Physical Review, 17(3): 273 (7 pages).

Xu, C. and Torres-Verdin, C., 2013 "Core-based petrophysical rock classification by quantifying pore-system orthogonality with a bimodal Gaussian density function". Mathematical Geosciences 45 (6) (6 pages).

* cited by examiner

SYSTEM AND METHOD OF TYPING HETEROGENEOUS RESERVOIR ROCKS

FIELD

The disclosure relates generally to the field of exploration and production of hydrocarbons and to a method of reservoir rock classification.

BACKGROUND

High-pressure mercury injection capillary pressure (MICP) testing is routinely used to evaluate core samples taken from heterogeneous reservoir rocks, such as carbonate rocks. These heterogeneous reservoir rocks have complex pore systems that require proper definition of the pore structure in order to obtain diagenetic history. MICP testing involves immersing a core sample in a pressure-sealed chamber, increasing the pressure in the chamber incrementally, and measuring the volume of mercury intruded into pore spaces in the sample at each pressure step. Larger pore throats will be invaded by mercury at lower pressures compared to smaller pore throats. The output data of MICP testing typically includes a capillary pressure curve, known as MICP curve, showing sample pore volume occupied by mercury as a function of increasing mercury intrusion pressure, and pore throat radius distribution. Core samples with different pore systems will produce different MICP curves and pore throat distributions, allowing MICP data to be used for rock typing.

Workflows for rock typing with MICP data typically include automatic clustering of MICP data to provide consistent rock typing results and mitigate the cognitive biases during the typing process. Workflows for rock typing with MICP data can be divided into two categories based on the differences in input to the clustering algorithms. One category of workflows uses key parameters of MICP curves that bear some physical meanings, such as entry pressure, pore throat aperture radii (R35) and pore throat sorting, and others, as input to the clustering algorithm (Bize-Forest et al., 2014). The other category of workflows develops mathematical models (e.g., bimodal Gaussian density functions, Lorentzian model, and Thomeer model) to fit the MICP data, and then obtains the fitting parameters as inputs for MICP clustering (Xu et al., 2013; Palavecino et al., 2016).

U.S. Patent No. 2016/0124115 (Theologou, et al., "A System and Method of Pore Type Classification for Petrophysical Rock Typing", 5 May 2016) describes a method of classifying rocks that involves selecting core samples from a reservoir and using a MICP device to acquire one or more datasets from the core samples. The method includes parameterizing the one or more datasets using a Gaussian error function and the MICP data to derive a plurality of curve fit parameters. The curve fit parameters are clustered to create one or more pore type groups. The pore type groups are extrapolated to all of the core samples and propagated to a well log domain for reservoir rock type classification. The method described in U.S. Patent No. 2016/0124115 falls under the category of workflows that develop a mathematical model to fit the MICP data and then obtain fitting parameters for MICP clustering. This approach does not analyze MICP data directly and may introduce bias and noise into the typing process.

SUMMARY

A method of rock typing includes obtaining MICP data regarding a region of interest, determining a plurality of distributions from the MICP data, constructing a distance matrix for the plurality of distributions using a statistical distance metric, generating a cluster tree of the plurality of distributions, adjusting the cluster tree based on a petrographic characteristic to produce an adjusted cluster tree, and determining pore structure types of the region of interest using the adjusted cluster tree. The statistical distance metric may be Wasserstein Distance. The cluster tree may be generated by hierarchical agglomerative clustering. The petrographic characteristic may be a number of rock types represented in the region of interest. The petrographic characteristic may be received as input. The adjusted cluster tree may be produced by partitioning the cluster tree to produce a number of clusters that matches the number of rock types. The plurality of distributions may be MICP curves. Alternatively, the plurality of distributions may be pore throat distributions. The adjusted cluster tree may be outputted to a well-log-based rock typing. The region of interest may be a carbonate reservoir. A plurality of core samples may be selected from the region of interest, and the MICP data may be acquired from the plurality of core samples using a MICP measurement device. A non-transitory computer-readable medium may include one or more sequences of instructions that when executed by at least one processor perform the method.

A method of rock typing includes selecting a plurality of core samples from a region of interest, acquiring MICP data from MICP testing of the plurality of core samples, obtaining a plurality of mercury saturation as a function of mercury injection pressure curves (MICP curves) from the MICP data, computing a distance matrix for the MICP curves using Wasserstein distance as a distance metric, generating a cluster tree of the MICP curves, extracting a number k of clusters from the cluster tree based on a number of rock types represented in the region of interest, wherein k>1 and k is an integer, and outputting the clusters to a well-log-based rock typing to classify pore structure types of the region of interest. The method may include performing a petrographic analysis of the plurality of core samples to identify a number m of depositional rock types represented in the region of interest, wherein the number k matches the number m. The cluster may be generated by hierarchical agglomerative clustering. A non-transitory computer-readable medium may include one or more sequences of instructions that when executed by at least one processor perform the method.

A non-transitory computer-readable medium includes one or more sequences of instructions that when executed by at least one processor cause the at least one processor to: obtain MICP data regarding a region of interest, determine a plurality of distributions from the MICP data, compute a distance matrix for the plurality of distributions using a statistical distance metric, generate a cluster tree of the plurality of distributions using the distance matrix, adjust the cluster tree based on a petrographic characteristic to produce an adjusted cluster tree, and determine pore structure types of the region of interest based on the adjusted cluster tree. The at least one processor may compute the distance matrix for the plurality of distributions using Wasserstein Distance as the statistical distance metric. The at least one processor may generate the cluster tree of the plurality of distributions using the distance matrix and hierarchical agglomerative clustering. The at least one processor may receive a number of rock types represented in the region of interest as the petrographic characteristic. The at least one processor may output the adjusted tree to a well-log-based rock typing.

The foregoing general description and the following detailed description are exemplary of the invention and are intended to provide an overview or framework for understanding the nature of the invention as it is claimed. The accompanying drawings are included to provide further understanding of the invention and are incorporated in and constitute a part of the specification. The drawings illustrate various embodiments of the invention and together with the description serve to explain the principles and operation of the invention.

BRIEF DESCRIPTION OF DRAWINGS

The following is a description of the figures in the accompanying drawings. In the drawings, identical reference numbers identify similar elements or acts. The sizes and relative positions of elements in the drawings are not necessarily drawn to scale. For example, the shapes of various elements and angles are not necessarily drawn to scale, and some of these elements may be arbitrarily enlarged and positioned to improve drawing legibility. Further, the particular shapes of the elements as drawn are not necessarily intended to convey any information regarding the actual shape of the particular elements and have been solely selected for ease of recognition in the drawing.

DETAILED DESCRIPTION

In the following detailed description, certain specific details are set forth in order to provide a thorough understanding of various disclosed implementations and embodiments. However, one skilled in the relevant art will recognize that implementations and embodiments may be practiced without one or more of these specific details, or with other methods, components, materials, and so forth. In other instances, well known features or processes associated with the hydrocarbon production systems have not been shown or described in detail to avoid unnecessarily obscuring descriptions of the implementations and embodiments. For the sake of continuity, and in the interest of conciseness, same or similar reference characters may be used for same or similar objects in multiple figures.

Figure 1:
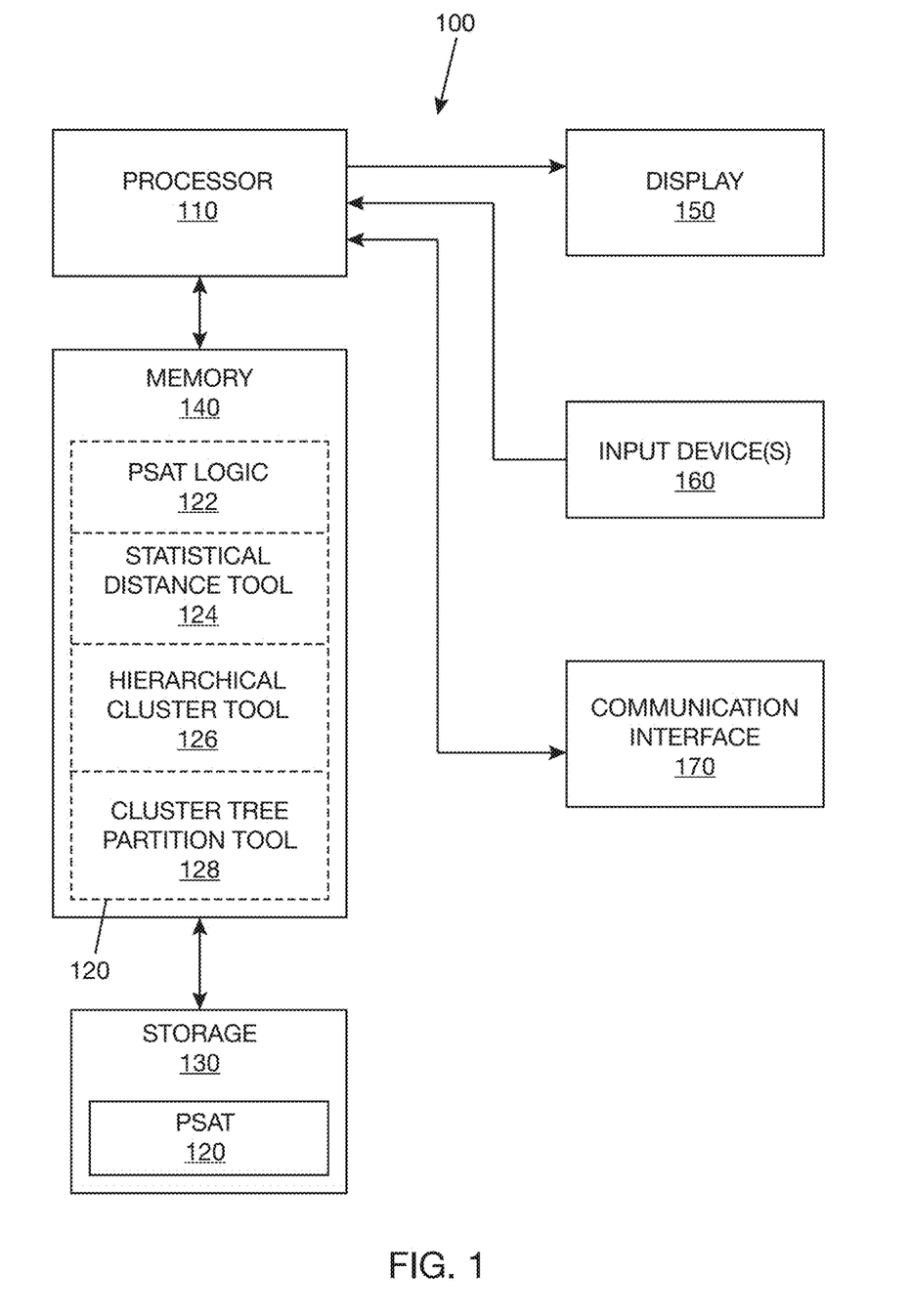
FIG. 1 is a schematic diagram of a rock typing system according to one illustrative implementation.

FIG. 1 is a schematic diagram of a rock typing system 100 according to one illustrative implementation. System 100 may include a processor 110 and a pore structure analysis toolbox (PSAT) 120 having instructions to be executed by processor 110. PSAT 120 may be stored in storage 130 and loaded into memory 140 for execution by processor 110. In one implementation, PSAT 120 includes PSAT logic 122, statistical distance tool 124, hierarchical cluster tool 126, and cluster tree partition tool 128. PSAT logic 122 manages the overall operation of PSAT 120. Statistical distance tool 124 includes logic to compute a distance matrix from mercury injection capillary pressure (MICP) data. Hierarchical cluster tool 126 includes logic to compose a cluster tree of the MICP data based on the distance matrix. Cluster tree partition tool 128 includes logic to partition the cluster tree into a desired number of clusters. During execution of PSAT 120, processor 110 receives or obtains the MICP data and a petrographic characteristic that guides partitioning of the cluster tree. Each MICP data cluster corresponds to a pore structure type. Processor 110 may provide the MICP data clusters to another process, e.g., a well-log-based rock typing, or to a reservoir modeling system. PSAT 120 provides a quick solution for pore structure parameter estimation and may be incorporated as a component of an integrated rock typing workflow for characterizing complex reservoirs.

Processor 110 may be any machine that performs computational operations. For example, processor may be a central processing unit (CPU), a microprocessor, a controller, an application specific integrated circuit (ASIC), system on chip (SOC), or a field-programmable gate array (FPGA). Each of storage 130 and memory 140 may be a non-transitory computer-readable storage medium that stores data and instructions and may include one or more of random-access memory (RAM), read-only memory (ROM), Flash memory, solid state drive, or other processor-readable storage medium. System 100 may include a display 150. A user interface of PSAT 120 may be presented on display 150 during execution of PSAT 120. System 100 may include input device(s) 160, such as a keyboard and mouse, to enable user interaction with a user interface presented on display 150. System 100 may include a communication interface 170 for connection to a network. System 100 may be a standalone system or may be a node on a network. In one example, system 100 may be implemented in a mobile laboratory. In another example, PSAT 120 may be stored in the cloud and accessed remotely from a computer. In this case, at least a portion of the instructions of PSAT 120 may be executed by a remote processor.

Figure 2:
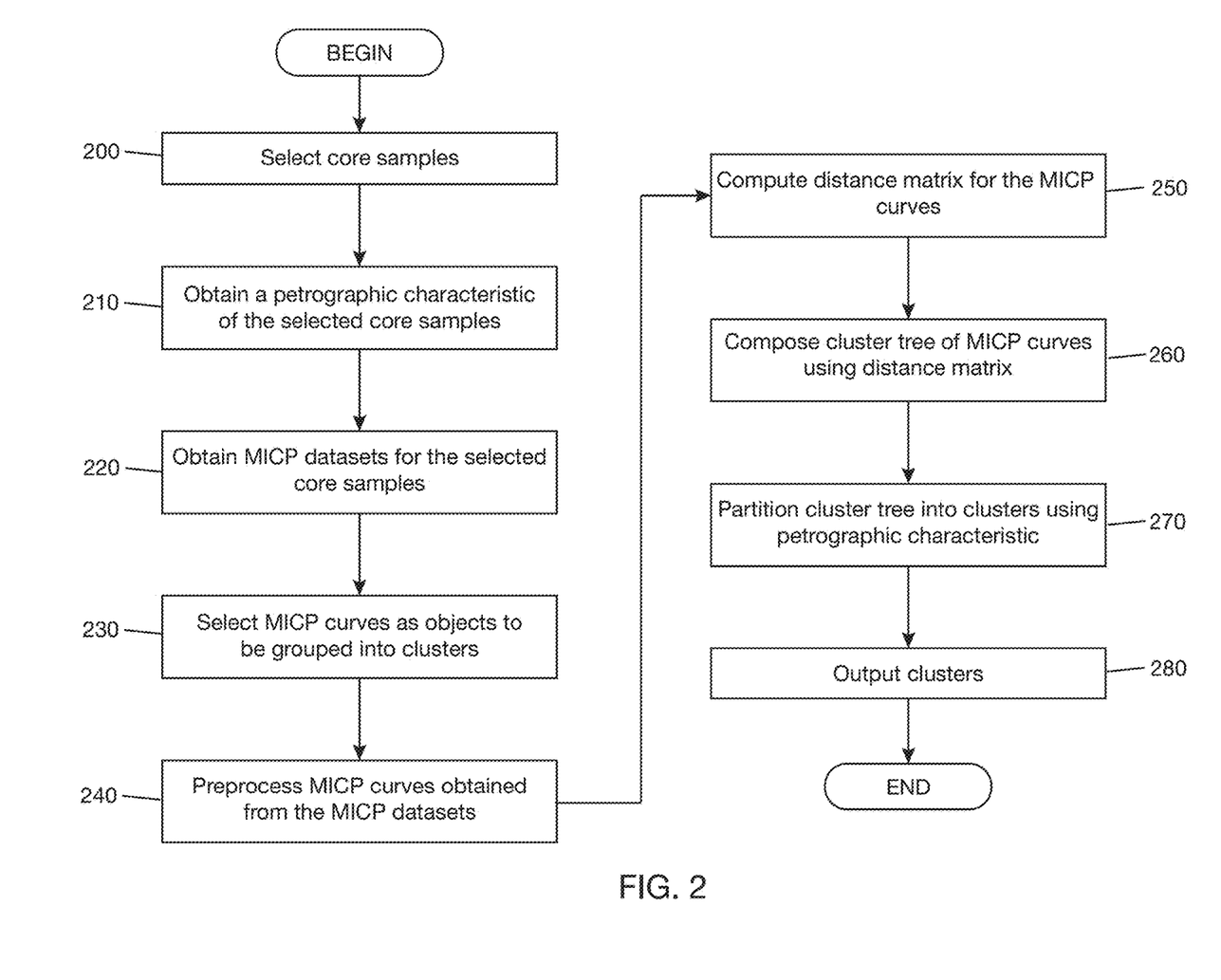
FIG. 2 is flow diagram showing a method of rock typing according to one illustrative implementation.

FIG. 2 is a flow diagram illustrating one implementation of a method of rock typing with PSAT (120 in FIG. 1). At 200, core samples from a region of interest are selected. Rock samples may be obtained from a wellbore by drilling the sides of the wellbore at the region of interest using a core bit. The region of interest may include a reservoir. The region of interest may include a carbonate reservoir. The rock samples are divided into sections, each of which provides a core sample. In some cases, the core samples may be cylindrical in shape, i.e., core plugs. However, the method is not limited to any particular shape of core sample. Practicing the method with PSAT and PSAT logic (122 in FIG. 1) may include the processor (110 in FIG. 1) receiving the selection of core samples. For example, a core sample dataset may describe the selection of core samples. The processor may receive the core sample dataset or may receive a memory location of the core sample dataset. In the latter case, the processor may retrieve the core sample dataset from the specified memory location. Alternatively, the processor may present a list of core sample datasets stored in one or more repositories on the display (150 in FIG. 1), a user may select a core sample dataset from the core sample dataset list, and the processor may receive the user selection of the core sample dataset.

At 210, a 'petrographic characteristic' of the region of interest is obtained. The petrographic characteristic is a characteristic of the region of interest based on petrographic analysis or observation of rock samples obtained from the region of interest. In one implementation, the petrographic characteristic of the region of interest is the number of depositional rock types represented in the region of interest. Depositional rock types may be based on deposition texture (e.g., grain/matrix ratio) and pore type. In one example, obtaining a petrographic characteristic of the region of interest may include preparing thin sections of core samples obtained from rocks in the region of interest. In one implementation, the core samples involved in the petrographic analysis are the same as the core samples selected at 210 or share parent rock samples with the core samples selected at 210. With the aid of a petrographic microscope or other petrographic analysis tool, the rocks and minerals present in the thin sections are identified and used to determine the number of depositional rock types. Practicing the method with PSAT (120 in FIG. 1) and PSAT logic (122 in FIG. 1) may include the processor (110 in FIG. 1) obtaining the petrographic characteristic from a specified memory location or receiving the petrographic characteristic as input.

At 220, MICP datasets (collectively, MICP data) for the selected core samples are obtained. The MICP datasets may be obtained by performing MICP tests on the selected core samples. Practicing the method with PSAT (120 in FIG. 1) and PSAT logic (122 in FIG. 1) may include the processor (110 in FIG. 1) obtaining MICP data acquired by performing MICP tests on the selected core samples. MICP tests are made on core samples with a mercury intrusion porosimeter or other MICP measurement device. In general, each MICP test includes immersing a respective core sample in a pressure-sealed chamber, increasing the pressure in the chamber in steps, and measuring the volume of mercury intruded into pore spaces in the sample at each pressure step. The pressure steps may be logarithmically-spaced steps. In a non-limiting example, injection pressures can range from approximately 1 psi to 60,000 psi during the tests, which would allow detection of pore throat sizes in the nanometer range.

Figure 3:
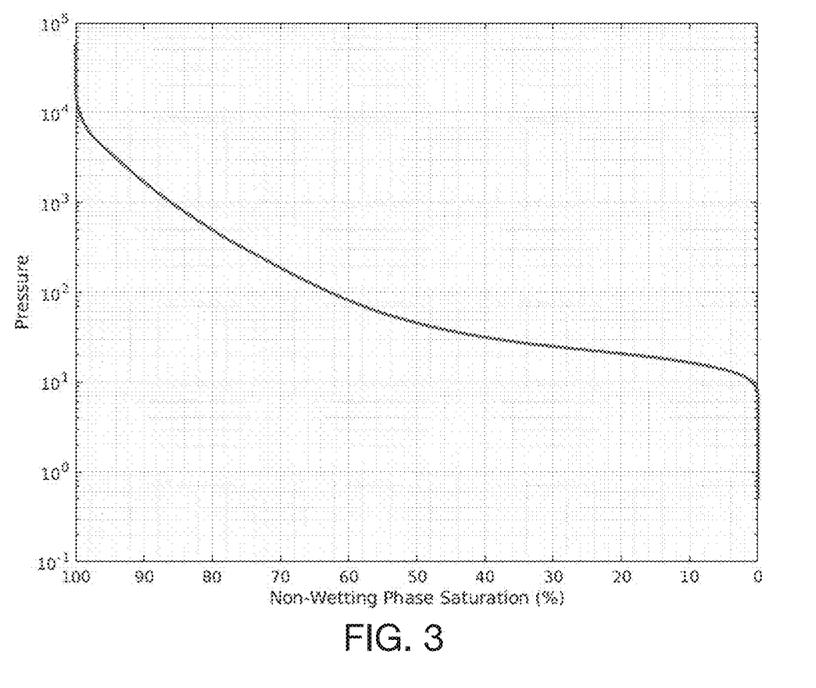
FIG. 3 is a plot of a MICP curve obtained by MICP testing of a rock sample.

MICP dataset for each core sample includes mercury intrusion data for each pressure step. A MICP curve for each core sample can be generated by fitting a curve to the MICP dataset. Typically, MICP curve is expressed as non-wetting phase saturation (sample pore volume occupied by mercury) as a function of mercury injection pressure (capillary pressure) on a semi-log plot. FIG. 3 shows an example of a MICP curve. For the core sample whose MICP curve is shown in FIG. 3, it can be observed that non-wetting phase saturation is at 0% until pressure is at about 10 psi. After 10 psi, non-wetting phase saturation starts to increase from 0%. The pressure at which mercury starts to intrude into the largest pore throats in a sample, which is when non-wetting phase saturation starts to increase from 0%, is known as the 'closure pressure'. In the example shown in FIG. 3, the closure pressure is about 10 psi, but the closure pressure will vary among core samples.

Pore throat distribution curve shows pore throat radius as a function of incremental mercury intrusion. Pore throat radius is not part of the MICP raw data. However, the external pressure required to force a non-wetting liquid, such as mercury, into a pore is inversely related to the pore radius. Thus, pore throat radius may be calculated, for example, using Washburn's equation (Washburn, 1921):

$$P_c = \frac{2\sigma\cos\theta}{r} \quad (1)$$

Figure 4:
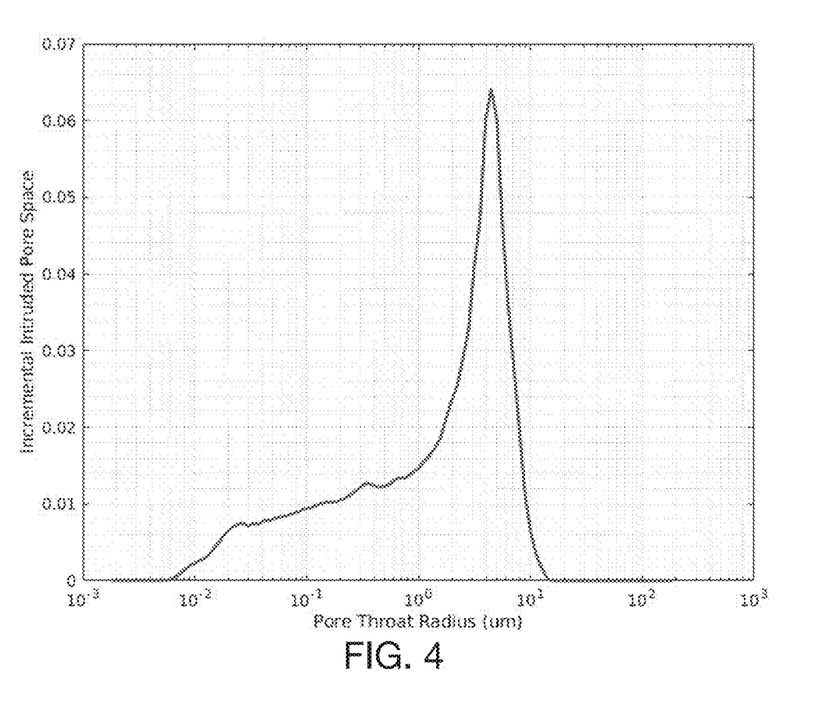
FIG. 4 is a plot of pore throat distribution corresponding to the MICP curve shown in FIG. 3.

In Equation (1), $P_c$ is the capillary pressure, $\sigma$ is the interfacial tension of mercury, $\theta$ is the contact angle between mercury and the pore surface, expressing wettability, and $r$ is the capillary radius (or pore throat radius). For illustrative purposes, FIG. 4 shows a pore throat distribution curve corresponding to the MICP curve shown in FIG. 3.

Returning to FIG. 2, at 230, MICP curves obtained from the MICP datasets are selected as rock objects to be grouped into clusters. Practicing the method with PSAT (120 in FIG. 1) and PSAT logic (122 in FIG. 1) may include the processor (110 in FIG. 1) extracting the MICP curves from the MICP data.

At 240, the MICP curves are preprocessed. Practicing the method with PSAT (120 in FIG. 1) and PSAT logic (122 in FIG. 1) may include the processor (110 in FIG. 1) preprocessing the MICP curves. The MICP curves may be preprocessed by applying a closure correction to each MICP curve. A closure correction removes mercury intrusion data up to the closure pressure from the MICP curve. For example, in FIG. 3, the data corresponding to 0% non-wetting phase saturation may be removed from the MICP curve. The MICP curves may be preprocessed by applying a smoothing function to each MICP curve. The MICP curves may be preprocessed by resampling the MICP curves so that all the MICP curves will have the same non-wetting phase saturation axis, i.e., non-wetting phase saturation is distributed from 0 to 100 with the same sampling interval.

Returning to FIG. 2, at 250, a distance matrix is computed for the MICP curves. Practicing the method with PSAT (120 in FIG. 1) and statistical distance tool (124 in FIG. 1) may include the processor (110 in FIG. 1) computing the distance matrix. A distance matrix is a square matrix containing the distances, taken pairwise, between the elements of a set. In this case, there is a set of MICP curves, each MICP curve in the set associated with one of the selected core samples. The computed distance matrix contains distances, taken pairwise, between the MICP curves. If there are N selected core samples, there will be N MICP curves in the set, and a distance matrix of size N×N. The distance between paired MICP curves is given by a statistical distance metric. In one example, the statistical distance metric used in computing the distance matrix is Wasserstein distance. Other examples of statistical distance metric include, but are not limited to, total variation distance and Kolmogorov-Smirnov distance.

Wasserstein distance (WD), also called Kantorovich-Monge-Rubinstein metric or Earth Mover's distance, is a distance function that is defined between two probability distributions on a metric space (Rubner et al., 2000; Ramdas et al., 2017). WD measures the minimum amount of work required to change one distribution into the other. Computing WD is itself an optimization problem.

Let $P_\theta(x)$ and $P_\gamma(y)$ represent two arbitrary discrete distributions. Suppose that $P_\theta(x)$ and $P_\gamma(y)$ describe the distribution of some mass. We try to find a transport plan $\gamma(x,y)$ that minimizes the total cost of transporting mass from $P_\theta(x)$ to $P_\gamma(y)$, or vice versa. To be a valid transport plan, $\gamma(x,y)$ is subject to the following constraints:

$$\int \gamma(x,y)d(x) = P_\gamma(y) \quad (2)$$

$$\int \gamma(x,y)d(y) = P_\theta(x) \quad (3)$$

In this case, γ(x,y) is a joined probability distribution whose marginals are $P_θ(x)$ and $P_γ(y)$. With this, WD can be defined as follows:

$$WD(P_θ, P_γ) = \inf_{γ \in π} \sum_{x,y} \|x-y\| γ(x,y) = \inf_{γ \in π} E_{(x,y) \sim γ} \|x-y\| \quad (4)$$

In Equation (4), the total cost of moving x toy is denoted as $\|x-y\|$. γ represents the transport plan, which is not unique. Equation (4) means that we calculate the expectation of total cost under the optimal transport plan γ. In other words, we need to find the optimal transport plan that minimizes the total cost of moving x to y. Equation (4) is a constraint optimization problem and can be calculated using the generic method of linear programming. If each MICP curve is treated as a distribution, then WD between each pair of MICP curves can be calculated by solving Equation (4). These WDs are recorded in the distance matrix computed at 250. The statistical distance tool (124 in FIG. 1) may be an algorithm that takes a set of distributions, in this case the set of MICP curves, as input and computes the distance matrix as described above.

For illustration purposes, let M be a set of six MICP curves labeled A to F. Table 1 shows an example representation of a distance matrix for M.

TABLE 1

|   | A | B | C | D | E | F |
|---|---|---|---|---|---|---|
| A | WD(A, A) | WD(A, B) | WD(A, C) | WD(A, D) | WD(A, E) | WD(A, F) |
| B | WD(B, A) | WD(B, B) | WD(B, C) | WD(B, D) | WD(B, E) | WD(B, F) |
| C | WD(C, A) | WD(C, B) | WD(C, C) | WD(C, D) | WD(E, D) | WD(C, F) |
| D | WD(D, A) | WD(D, B) | WD(D, C) | WD(D, D) | WD(D, E) | WD(D, F) |
| E | WD(E, A) | WD(E, B) | WD(E, C) | WD(E, D) | WD(E, E) | WD(E, F) |
| F | WD(F, A) | WD(F, B) | WD(F, C) | WD(F, D) | WD(F, E) | WD(F, F) |

The distance between the same MICP curve should be 0. Thus, WD(i,i)=0 for all i in M. Also, the distance between the same pair of MICP curves should be the same regardless of the direction in which "mass" is transported between the MICP curves. Thus, WD(i,j)=WD(j,i) for all i,j in M. Thus, the distance matrix in Table 1 could be rewritten as shown in Table 2.

TABLE 2

|   | A | B | C | D | E | F |
|---|---|---|---|---|---|---|
| A | 0 | WD(A, B) | WD(A, C) | WD(A, D) | WD(A, E) | WD(A, F) |
| B | WD(A, B) | 0 | WD(B, C) | WD(B, D) | WD(B, E) | WD(B, F) |
| C | WD(A, C) | WD(B, C) | 0 | WD(C, D) | WD(E, D) | WD(C, F) |
| D | WD(A, D) | WD(B, D) | WD(C, D) | 0 | WD(D, E) | WD(D, F) |
| E | WD(A, E) | WD(B, E) | WD(C, E) | WD(D, E) | 0 | WD(E, F) |
| F | WD(A, F) | WD(B, F) | WD(C, F) | WD(D, F) | WD(E, F) | 0 |

At 260 in FIG. 2, a cluster tree or dendrogram of the MICP curves is composed using the distance matrix. Practicing the method with PSAT (120 in FIG. 1) and hierarchical cluster tool (126 in FIG. 1) may include the processor (110 in FIG. 1) receiving the distance matrix and MICP curves as input and composing the cluster tree. In one implementation, hierarchical agglomerative clustering (HAC) is used to compose the cluster tree. HAC is a type of bottom-up hierarchical clustering. The cluster tree has a multilevel hierarchical structure. By considering each MICP curve as its own singleton cluster, in an iterative process, the pairs of MICP curves with the highest similarity values are identified and merged into groups. This process is repeated until all items have been merged into one group. This is illustrated in FIGS. 5A-5D. If the number of MICP datasets is represented by n and the number of clusters is represented by k, then the time complexity of hierarchical algorithm is $O(kn^2)$. In this way, hierarchical clustering does not provide a single clustering of the data, but provides n-1 clustering of the data.

At each step of HAC, the two clusters separated by the shortest distance are combined. There are various methods of defining shortest distance (or cluster proximity), such as single linkage, complete linkage, average linkage, and centroid linkage. In single-linkage, clustering, also known as nearest neighbor clustering, the distance between two clusters is defined as the shortest distance between a pair of objects, where the pair is made up of one object from each cluster. In complete-linkage clustering, also known as farthest neighbor clustering, the distance between two clusters is defined as the farthest distance between a pair of objects, where the pair is made up of one object from each cluster. In average-linkage clustering, the distance between two clusters is defined as the average of the distances between all pairs of objects, where each pair is made up of one object from each cluster. In centroid-linkage clustering, also known as Ward's method, cluster proximity is defined by the distance between the centroids of two clusters.

Figure 5A:
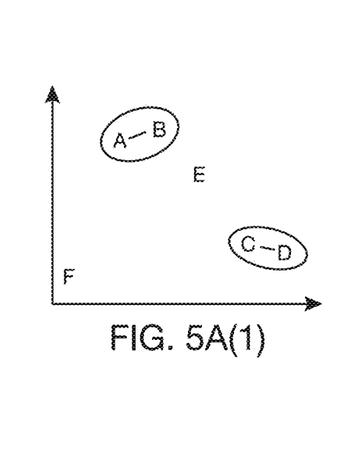
FIGS. 5A-5D illustrate a process of hierarchical agglomerative clustering.
Figure 5B:
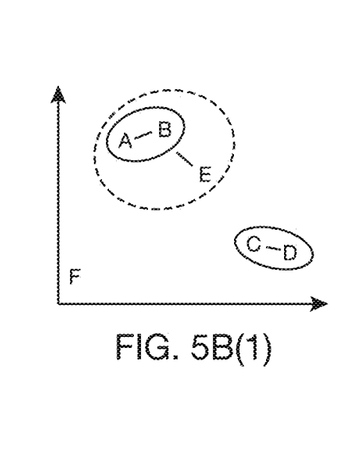
Figure 5C:
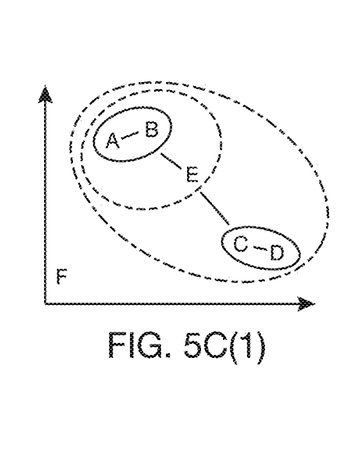

Assume that before a first clustering step the distance matrix is as shown in Table 2. Further assume, for illustrative purposes, that a first clustering step is performed as shown in FIGS. 5A(1) and 5A(2). In the example of FIGS. 5A(1) and 5A(2), clusters A and B are merged into a single cluster (A, B), and clusters C and D are merged into a single cluster (C, D). The active clusters after the first clustering step are (A,B), E, (C,D), and F. After this first clustering step, the distance matrix will be updated. Table 3 shows an update to the distance matrix based on single-linkage clustering. (Single-linkage clustering has been selected for ease of illustration. However, other methods of clustering may be used to update the distance matrix. In some cases, these other methods, such as average-linkage clustering and Ward's method, may be preferred to avoid elongated clusters commonly produced by single-linkage clustering.)

TABLE 3

|   | (A,B) | (C,D) | E | F |
|---|---|---|---|---|
| (A,B) | 0 | min(WD(A,C), WD(A,D), WD(B,C), WD(B,D)) | min(WD(A,E), WD(B,E)) | min(WD(A,F), WD(B,F)) |
| (C,D) | min(WD(A,C), WD(A,D), WD(B,C), WD(B,D)) | 0 | min(WD(C,E), WD(D,E)) | min(WD(C,F), WD(D,F)) |
| E | min(WD(A,E), WD(B,E)) | min(WD(C,E), WD(D,E)) | 0 | WD(E,F) |
| F | min(WD(A,F), WD(B,F)) | min(WD(C,F), WD(D,F)) | WD(E,F) | 0 |

Figure 5D:
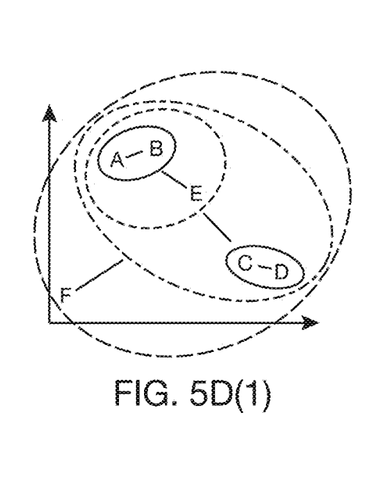

Using the updated distance matrix, a second clustering step can be performed. For illustrative purposes, FIGS. 5B(1) and 5B(2) show that clusters (A,B) and E are merged into a single cluster ((A,B), E). The active clusters after the second clustering step are ((A,B), E), (C,D), and F. Again, the distance matrix can be updated for the next clustering step. The clustering algorithm runs until all the clusters have been merged into a single cluster, as illustrated in FIGS. 5D(1) and 5D(2).

Figure 6:
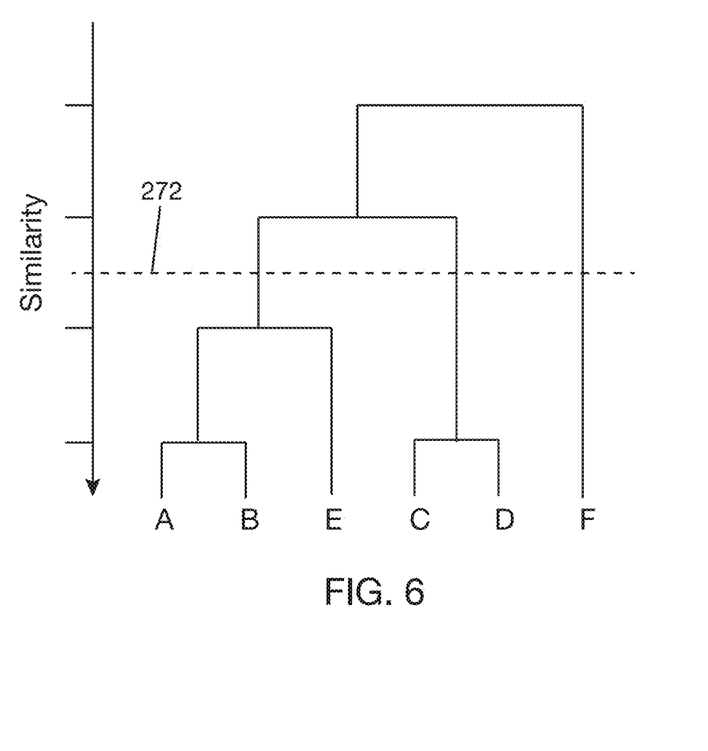
FIG. 6 illustrates cutting of a cluster tree.

At 270, the cluster tree obtained at 260 is partitioned to obtain a number k>1 of clusters. In one implementation, the number of clusters is determined by the petrographic characteristic obtained at 210. In one implementation, the petrographic characteristic indicates the number of depositional rock types represented in the MICP data. Practicing the method with PSAT (120 in FIG. 1) and cluster tree partition tool (128 in FIG. 1) may include the processor (110 in FIG. 1) receiving the cluster tree and the petrographic characteristic as input and outputting the number of clusters that match the number of depositional rock types. Partitioning can be visualized as cutting the cluster tree at a certain height (corresponding to a similarity threshold) to produce the desired number of clusters. For example, FIG. 6 shows a cut line 272 to produce three clusters from the cluster tree previously shown in FIG. 5D(2). The resulting clusters would be ((A,B),E), (C,D), and F. Partitioning can be accomplished with statistical computing tools such as R (RDocumentation, www.rdocumentation.org). For example, R has a function cutree(tree, k=NULL, h=NULL), where tree is a cluster tree, k is an integer scalar or vector with the desired number of groups, and h is a numeric scalar or vector with heights where the tree should be cut. At least one of k and h must be specified. This function can be called with a cluster tree and the petrographic characteristic as the desired number of groups. Alternatively, a plot of the cluster tree could be generated (as shown in FIG. 6), and a height at which the tree should be cut can be determined from the plot. Then, the function can be called with a cluster tree and a height.

Returning to FIG. 2, at 280, the clusters produced at 270 are outputted. Practicing the method with PSAT (120 in FIG. 1) may include the processor (110 in FIG. 1) receiving the clusters from the cluster tree partition tool (128 in FIG. 1) and outputting the clusters. The clusters may be displayed, stored, or provided to another program. Each cluster represents a MICP type. The MICP types reveal pore structure types. Thus, the clusters can be used to determine pore structure types in the region of interest. The clusters may be provided as input to a well-log-based rock typing, which then uses the clusters to provide distributions of rock types that are suitable for reservoir modeling and simulation. Well-log-based rock typing refers to classification of rock types in the reservoir based on petrophysical, elastic, and compositional properties provided by well log data (e.g., compressional and shear-wave slowness, density, neutron, and nuclear magnetic resonance). The MICP based rock typing results can be used as calibration points of well log scale rock typing. In other words, the MICP based rock types are used as ground truth for well-log-based rock typing. Both MICP based rock typing and well-log-based rock typing can be part of an integrated rock-typing workflow for characterizing complex reservoirs.

Figure 7:
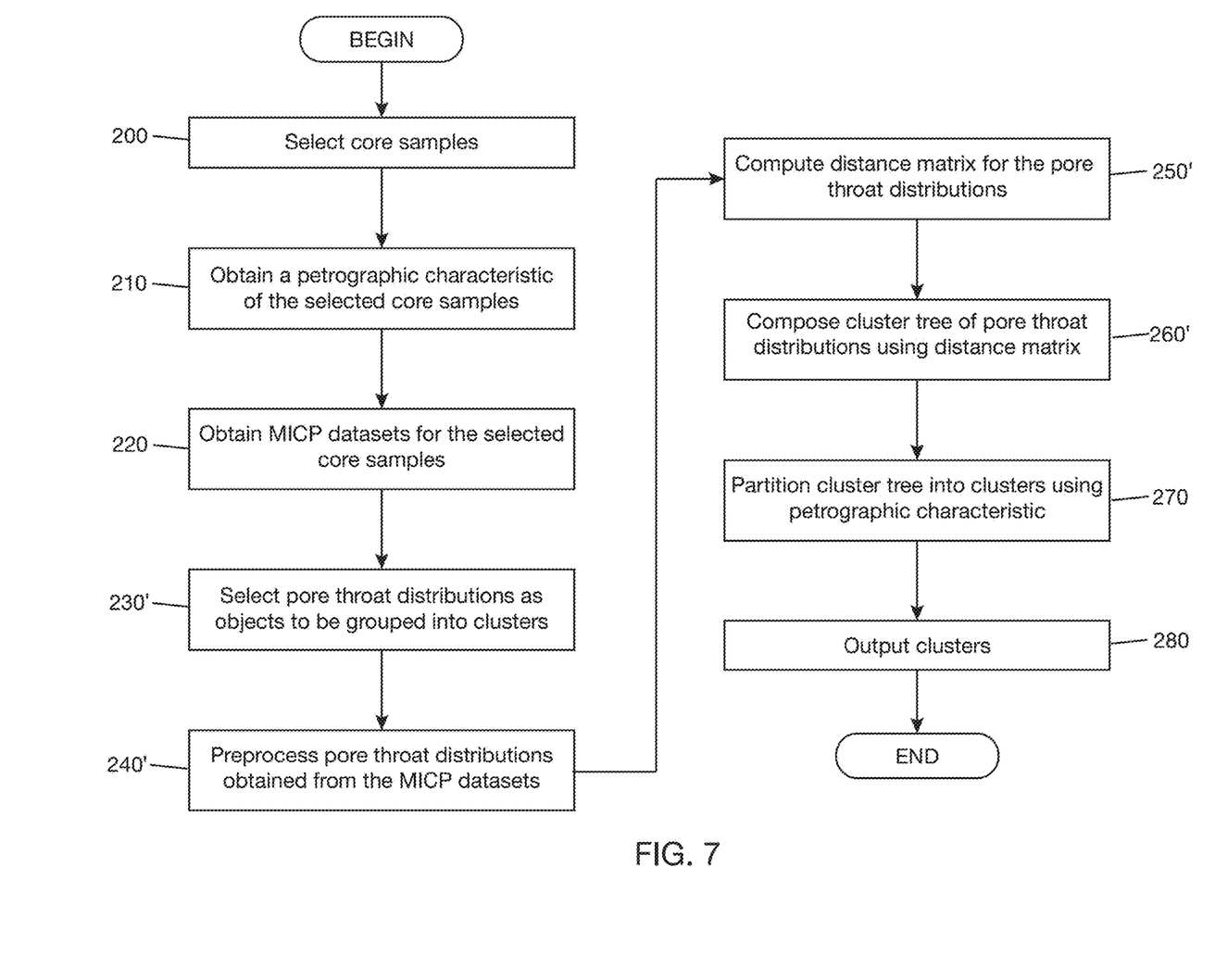
FIG. 7 is a flow diagram showing a method of rocking typing according to another illustrative implementation.

The method of rock typing of FIG. 2 has been described with respect to clustering MICP curves. In another implementation, pore throat distributions may be clustered instead of MICP curves. FIG. 7 shows the method of FIG. 2 modified for clustering of pore throat distributions. That is, at 230', pore throat distributions are selected as objects to be grouped into clusters; at 240', pore throat distributions obtained from the MICP datasets may be preprocessed; at 250', a distance matrix may be computed for the pore throat distributions, and computation of the distance matrix may be based on WD or other statistical distance metric; and at 260', a cluster tree of pore throat distributions may be composed using the distance matrix. 200, 210, 270, and 280 in FIG. 7 may be the same as in FIG. 2. In general, any distribution measures that may be derived from MICP data may be clustered by the method described in FIG. 2.

EXAMPLE 1

Twenty-one core samples were selected.

EXAMPLE 2

Petrographic analysis was performed on the core samples of Example 1. The analysis revealed carbonate rocks composed of grainstone, mud-lean packstone, packstone, wackestone, and mudstone. Three reservoir rock types were identified. Type I rock type had a grain-supported texture with or without micritic matrix and intergranular pore domination. Type II rock type was dominated by packstones with significant amounts of matrix (poorly peloids and ooids were the major grain types) and intergranular pore domination. Type III rock type was composed of compositionally micritic mud-dominated wackestone and mudstone with dissolution pores.

EXAMPLE 3

Figure 8:
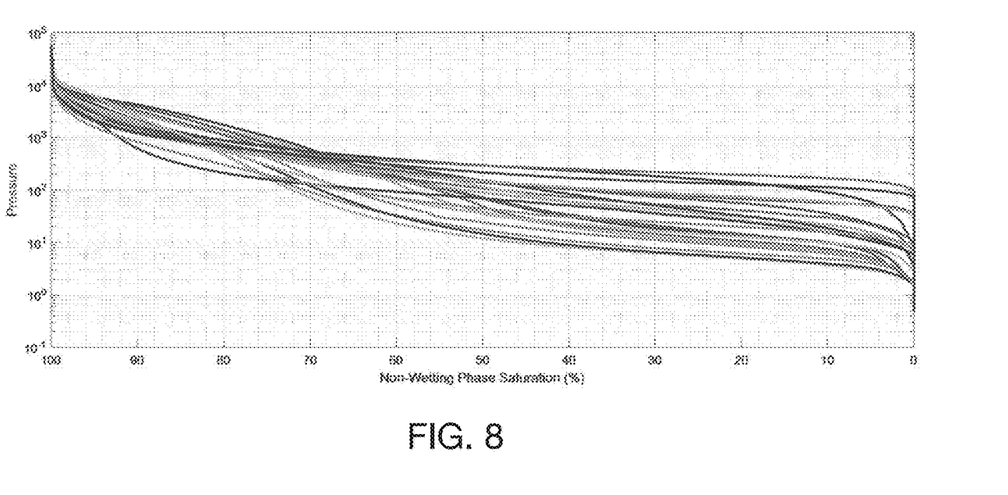
FIG. 8 is a plot of MICP curves obtained by MICP testing of core samples according to one example.
Figure 9:
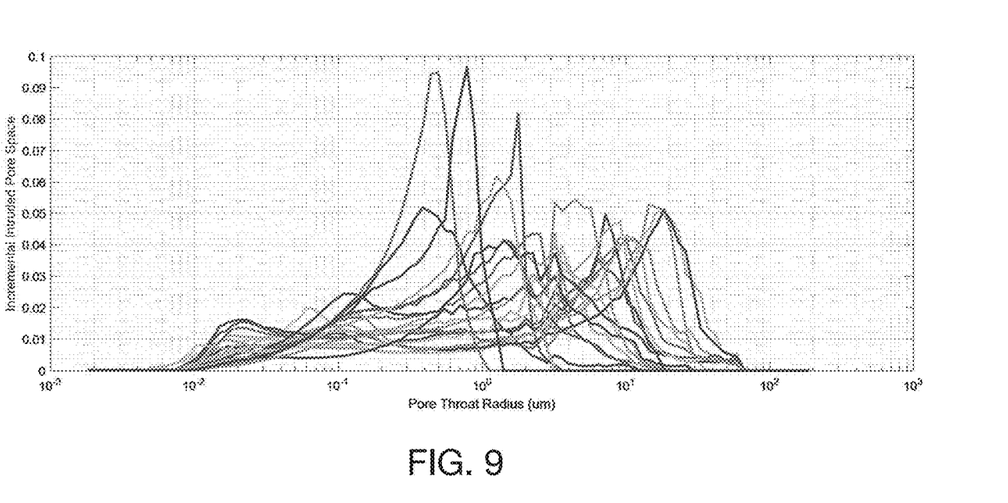
FIG. 9 is a plot of pore throat distributions corresponding to the MICP curves shown in FIG. 8.
Figure 10A:
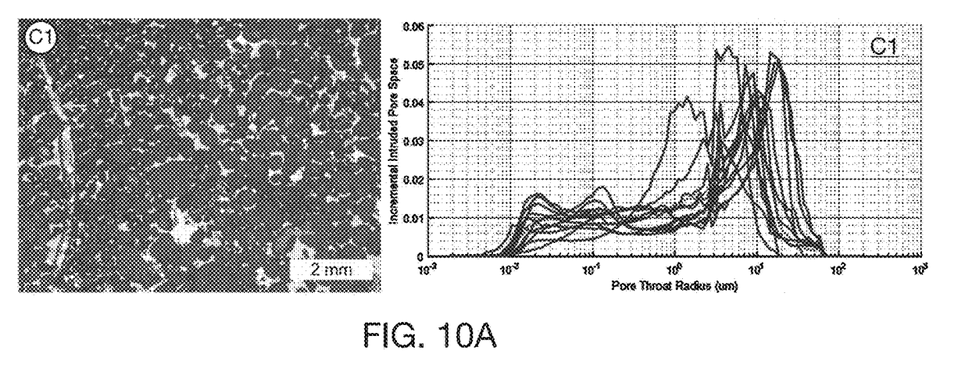
FIGS. 10A-10C show clusters produced by applying the method of FIG. 2 to a selection of core samples.
Figure 10B:
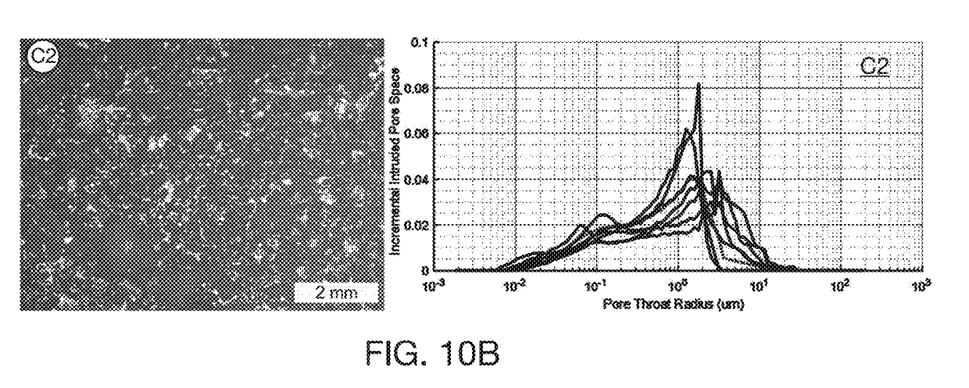
Figure 10C:
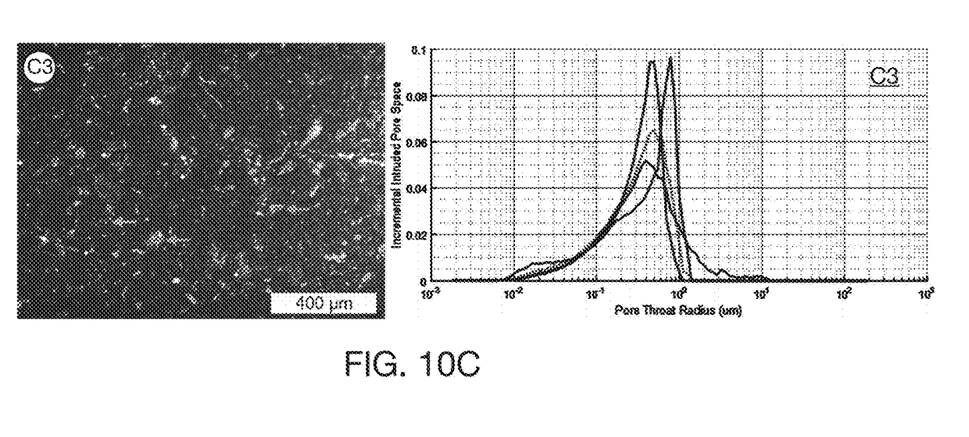

A method of rock typing according to 210 to 280 in FIG. 2 was performed on the core samples of Example 1. FIGS. 8 and 9 show the MICP curves and corresponding pore throat distributions, respectively. The petrographic characteristic was three based on the number of rock types identified in Example 2. Three clusters were outputted. FIGS. 10A-10C show pore throat distributions for the three clusters C1, C2, C3 and corresponding grain structures. Cluster C1 rocks (in FIG. 10A) had the largest pore throat with a major peak at approximately 10 μm, which is consistent with the fact that the pore space is dominated by large intergranular pores. In Cluster C2 (in FIG. 10B), much of the intergranular space was filled with matrix and fine-sized grains, which makes Cluster C2 rocks contain less visible open pores in comparison with Cluster C1 rocks. This feature was also validated by the MICP derived pore throat distribution. The major peak of Cluster C2 rocks was at approximately 1 μm. In contrast to the rocks of Cluster C1 and Cluster C2, the visible open pores in Cluster C3 rocks (in FIG. 10C) are minor and most of them originate mainly from dissolution of existing grains. The MICP derived pore throat distribution exhibited a narrow range, and the major peak was approximately 0.5 µm. The results show consistency between the clusters outputted by the method and the rock types identified in Example 2.

While the invention has been described with respect to a limited number of embodiments, those skilled in the art, having the benefit of this disclosure, will appreciate that other embodiments can be devised that do not depart from the scope of the invention as described herein. Accordingly, the scope of the invention should be limited only by the accompanying claims.

REFERENCES

Bize-Forest, N., Baines, V. Boyd, A., Moss, A., & Olivieria, A. (2014). Carbonate Reservoir Rock Typing and the Link between Routine Core Analysis. International Symposium of the Society of Core Analysts, pp. 8-11.

Xu, C. & Torres-Verdin, C. (2013). Core-Based Petrophysical Rock Classification by Quantifying Pore-System Orthogonality with a Bimodal Gaussian Density Function. *Mathematical Geosciences*, 45(6), 753-771.

Palavecino, M. & Torres-Verdin, C. (2016). New Method of Petrophysical Rock Classification Based on MICP and Grain-Size Distribution Measurements. SPWLA 57$^{th}$ Annual Logging Symposium.

Washburn, E. W. (1921). The Dynamics of Capillary Flow. *Physical Review*, 17(3), 273.

Rubner, Y., Tomasi, C., and Guibas, L. J. (2000). The Earth Mover's Distance as a Metric for Image Retrieval. *International Journal of Computer Vision*, 40(2), 99-121.

Ramdas, A., Garcia, N., and Cuturi, M. (2017). On Wasserstein Two Sample Testing and Related Families of Nonparameteric Tests. *Entropy*, 19(2), 47.

What is claimed is:

1. A method of rock typing comprising:
    selecting a plurality of core samples from a region of interest;
    obtaining, by a computer processor, mercury injection capillary pressure (MICP) data regarding the region of interest from the plurality of core samples using an MICP measurement device;
    determining, by the computer processor, a plurality of distributions from the MICP data;
    computing, by the computer processor, a distance matrix for the plurality of distributions using a statistical distance metric;
    generating, by the computer processor and using the distance matrix, a cluster tree of the plurality of distributions;
    performing a petrographic analysis of the plurality of core samples to identify a number m of rock types represented in the region of interest;
    adjusting, by the computer processor, the cluster tree using as input the number m of rock types to produce an adjusted cluster tree; and
    determining pore structure types of the region of interest based on the adjusted cluster tree.

2. The method of claim 1, wherein the statistical distance metric is Wasserstein Distance.

3. The method of claim 2, wherein generating, by the computer processor and using the distance matrix, a cluster tree of the plurality of distributions comprises generating the cluster tree by hierarchical agglomerative clustering.

4. The method of claim 1, wherein adjusting, by the computer processor, the cluster tree based on the petrographic characteristic to produce the adjusted cluster tree comprises partitioning the cluster tree to produce a number of clusters that matches the number of rock types.

5. The method of claim 1, wherein the plurality of distributions are MICP curves.

6. The method of claim 1, wherein the plurality of distributions are pore throat distributions.

7. The method of claim 1, further comprising outputting, by the computer processor, the adjusted cluster tree to a well-log-based rock typing.

8. The method of claim 1, wherein the region of interest comprises a carbonate reservoir.

9. A method of rock typing comprising:
    selecting a plurality of core samples from a region of interest;
    acquiring mercury injection capillary pressure (MICP) data from MICP testing of the plurality of core samples;
    obtaining a plurality of mercury saturation as a function of mercury injection pressure curves (MICP curves) from the MICP data;
    computing a distance matrix for the MICP curves using Wasserstein distance as a distance metric;
    generating a cluster tree of the MICP curves;
    performing a petrographic analysis of the plurality of core samples to identify a number m of rock types represented in the region of interest;
    extracting a number k of clusters from the cluster tree based on a number of m of rock types represented in the region of interest, wherein k>1, and wherein the number k matches the number m; and
    outputting the clusters to a well-log-based rock typing to classify pore structure types of the region of interest.

10. The method of claim 9, wherein generating the cluster tree of the MICP curves comprises generating the cluster tree by hierarchical agglomerative clustering.

11. A non-transitory computer-readable medium including one or more sequences of instructions that when executed by at least one processor to perform the method recited in claim 9.

12. A non-transitory computer-readable medium including one or more sequences of instructions that when executed by at least one processor cause the at least one processor to:
    obtain mercury injection capillary pressure (MICP) data from an MICP measurement device regarding a region of interest;
    determine a plurality of distributions from the MICP data;
    compute a distance matrix for the plurality of distributions using a statistical distance metric;
    generate a cluster tree of the plurality of distributions using the distance matrix;
    receive as input a number m of rock types obtained from a petrographic analysis of a plurality of core samples from the region of interest;
    adjust the cluster tree based on the number m of rock types to produce an adjusted cluster tree; and
    determine pore structure types of the region of interest based on the adjusted cluster tree.

13. The non-transitory computer-readable medium of claim 12, wherein the at least one processor computes the distance matrix for the plurality of distributions using Wasserstein Distance as the statistical distance metric.

14. The non-transitory computer-readable medium of claim 13, wherein the at least one processor generates the cluster tree of the plurality of distributions using the distance matrix and hierarchical agglomerative clustering.

15. The non-transitory computer-readable medium of claim 13, further comprising the at least one computer processor outputting the adjusted tree to a well-log-based rock typing.

\* \* \* \* \*